United States Patent [19]

Tanizaki et al.

[11] 3,957,667

[45] May 18, 1976

[54] HYDRAULIC OIL COMPOSITION

[75] Inventors: Yoshiharu Tanizaki, Kamakura; Hiroshi Kawaguchi, Tokyo; Kenichiro Minagawa, Kawasaki, all of Japan

[73] Assignee: Nippon Oils and Fats Company Limited, Tokyo, Japan

[22] Filed: Dec. 23, 1974

[21] Appl. No.: 536,950

[30] Foreign Application Priority Data

Dec. 29, 1973  Japan.................................. 49-2350

[52] U.S. Cl. .................................................. 252/73
[51] Int. Cl.² ........................ C09K 3/00; C10M 3/22
[58] Field of Search ................................. 252/73–75

[56] References Cited
UNITED STATES PATENTS

| | | |
|---|---|---|
| 2,520,611 | 8/1950 | Roberts et al. .................. 252/73 X |
| 3,062,747 | 11/1962 | Fife et al............................. 252/73 |
| 3,287,274 | 11/1966 | Edwards et al. ..................... 252/73 |
| 3,329,614 | 7/1967 | Milnes et al. ..................... 252/73 X |
| 3,346,501 | 10/1967 | Boehmer............................. 252/73 |
| 3,472,781 | 10/1969 | Ziemba............................ 252/73 X |
| 3,528,920 | 9/1970 | Niizeki et al......................... 252/73 |
| 3,629,111 | 12/1971 | Cramer................................ 252/75 |

*Primary Examiner*—Harris A. Pitlick
*Attorney, Agent, or Firm*—Stevens, Davis, Miller & Mosher

[57] ABSTRACT

A hydraulic oil composition for automobile, comprising low molecular weight polyoxyalkylene glycol monoalkyl ether and dialkyl ether and a high molecular weight polyoxyalkylene compound. The hydraulic oil composition has improved low temperature viscosity characteristics and fluidity and has a low swelling action on rubber.

4 Claims, No Drawings

HYDRAULIC OIL COMPOSITION

The present invention relates to a polyoxyalkylene glycol type hydraulic oil, and more particularly relates to a hydraulic oil composition for automobile, which is composed of three components of a monoalkyl ether of low molecular weight polyoxyalkylene glycol (hereinafter, referred to as PAG), a dialkyl ether of PAG and a high molecular weight polyoxyalkylene compound.

In America, DOT Standard, which defines brake oils having more improved quality than the quality defined in SAE Standard, has been established, and DOT-3 STandard has been enforced in Mar. 1, 1972. Further, DOT-4 Standard has been proposed in order to define brake oils having more improved quality.

In Japan, as the brake oil for automobile, a JIS, No. 1-1 type brake oil composed mainly of vegitable oil (castor oil) and a JIS, No. 2-2 type oil composed of polyoxyalkylene glycol and having a high performance, are widely used.

The PAG type synthetic hydraulic oil has excellent properties to be used as a lubricating oil. That is, the oil (1) has a high viscosity index, (2) is stable chemically (3) is excellent in the shear stability, (4) is poor in the compatibility with sealing materials, such as natural rubber, SBR, etc. and does not swell the sealing materials, and (4) is stable against oxidation and does not form sludge, varnish, etc. Therefore, the PAG type synthetic hydraulic oils are mostly used as a brake oil of automobile and are partly used as a water-glycol type hydraulic oil. However, their performances are still insufficient.

The hydraulic oil composition of the present invention has excellent properties to be used not only as a hydraulic oil of brake, but also as a hydraulic oil of suspension (shock absorber) and as a autotransmission fluid (ATF). Further, the hydraulic oil composition can be advantageously used as a hydraulic oil for use in applications such as power steering units, seat actuators, windshield wipers, window regulators or the like.

The present invention provides a hydraulic oil composition comprising 100 parts by weight of a mixture of 60–98% by weight of PAG monoalkyl ether having the following general formula (1) and 2.0–40% by weight of at least one of PAG dialkyl ethers having the follwing general formulae (2) and (3),

and

wherein $R^1$ and $R^2$ represent alkyl groups having 1–3 carbon atoms respectively, $C_mH_{2m}O$ represents an oxyalkylene group, $m$ represents a positive intager of 2, 3 or 4, and n represents a positive integer of 2–6, the oxyethylene content in the total oxyalkylene of compounds (1), (2) and (3) being 40–90% by weight, and 2–40 parts by weight of a high molecular weight polyoxyalkylene compound having a kinematic viscosity of at least 8 cst at 210°F and having not less than 90% by weight of polyoxyalkylene glycol in the molecule and 15–80% by weight of oxyethylene based on the total oxyalkylene in the molecule.

In the present invention, PAG dialkyl ether having a low molecular weight is used as one component of PAG type hydraulic oils, whereby hydraulic oils having an improved viscosity characteristics, particularly having an improved fluidity and a low viscosity at low temperature, can be obtained.

The PAG monoalkyl ether (1) is prepared by a random or block addition polymerization of ethylene oxide (hereinafter, referred to as EO), propylene oxide (PO) and butylene oxide (BO) to methanol, ethanol, n-propyl alcohol or isopropannol at a temperature of 60°–160°C in the presence of an alkali metal compound as a catlyst.

The PAG dialkyl ethers (2) and (3) are prepared in the following manner. An alkali metal compound, for example, metallic sodium, sodium methylate, sodium hydroxide or potassium hydroxide, is added to PAG monoalkyl ether (1) to convert the terminal OH group of the monoether into alkali metal salt through dehydrogenation reaction, alcohol-forming reaction from the alkali metal alcoholate or dehydration reaction, and then methyl chloride ($CH_3Cl$), ethyl chloride or propyl chloride is added to the alkali metal salt to effect an alkyl-etherifying reaction, whereby the PAG dialkyl ether (2) is obtained. When methylene chloride ($CH_2Cl_2$) is added to the alkali metal salt of the monoether, the PAG dialkyl ether (3) is obtained.

The mixture of PAG monoalkyl ether (1) and PAG dialkyl ether (2) or (3) can be obtained by mixing the compounds in a given ratio. Alternatively, when the terminal OH group of the compound (1) is partially alkyl-etherified in the production of the compound (2) or (3) so that the alkyl-etherification rate is 2–40%, the aimed mixture of PAG monoalkyl ether (1) and PAG dialkyl ether (2) or (3) can be obtained.

The high molecular weight poloxyalkylene compound having a kinematic viscosity of at least 8 cst at 210°C can be obtained by a random addition polymerization of alkylene oxide (AO) to a compound having active hydrogen, for example, aliphatic alcohol or amine, at 80°–140°C in the presence of an alkali metal compound as a catalyst.

As the active hydrogen-containing compound, lower monohydric alcohols, such as methanol, ethanol, butanol, etc., are preferably used. However, dihydric alcohols, such as ethylene glycol, propylene glycol, butylene glycol, etc., or trihydric alcohols, such as glycerine, trimethylolpropane, etc. can be also used.

Further, as the high molecular weight polyoxyalkylene compound, modified polyoxyalkylene compound, which is obtained by alkyl-ethyrifying or esterifying the terminal OH group of the poloxyalkylene compound obtained by the addition polymerization of AO to the active hydrogen-containing compound, or modified polyoxyalkylene compound having oxymethylene groups in the molecule, which is obtained by reacting methylene dihalogenide or formaldehyde with the terminal OH group of the above obtained polyoxyalkylene compound according to the method described in U.S. Pat. Nos. 2,813,129 and 2,976,923, may be used.

In the present invention, compounds (2) and/or (3) are added to compound (1) in an amount of 2–40% by weight based on the total amount of the resulting mixture in order to improve the viscosity characteristics and fluidity at low temperature of the aimed hydraulic oil. When the amount of compounds (2) and/or (3) is less than 2% by weight, a satisfactory effect can not be attained. While, when the amount is more than 40%, the swelling action of the resulting hydraulic oil on sealing material (rubber) is high.

In the present invention 60–98% by weight of PAG monoakyl ether (1) is necessary as a base oil. The reason why the terminal group of the compound (1) is limited to methyl, ethyl or propyl group is that, when the terminal group is butyl group or a group higher than butyl group, the swelling action of the resulting hydraulic oil on rubber is high. Further, the reason why the oxyethylene content in the total oxyalkylene of compound (1) and compounds (2) and/or (3) is limited to 40–60% by weight is that, when the oxyethylene content is less than 40% by weight, the swelling action of the resulting hydraulic oil on rubber is high and further the hydraulic oil is poor in the low temperature viscosity characteristics and is apt to have a low wet equilibrium reflex boiling temperature. While, when the oxyethylene content is more than 90% by weight, the resulting hydraulic oil is apt to be solidified at low temperature and is poor in the fluidity at low temperature.

The reason why 2–6 moles of AO is added to alcohol is that, when less than 2 moles of AO is added, the boiling point and flash point of the resulting hydraulic oil are decreased, while when more than 6 moles of AO is added, the resulting hydraulic oil is poor in the low temperature viscosity characteristics and fluidity.

The reason why the kinematic viscosity of the high molecular weight polyoxyalkylene compound is limited to at least 8 cst, preferably 20–50,000 cst, at 210°F is that at least 8 cst of kinematic viscosity of the polyoxyalkylene compound is necessary in order to improve the viscosity index of the resulting hydraulic oil. When the kinematic viscosity thereof is more than 50,000, the resulting hydraulic oil is poor in the fluidity and in the shear stability at low temperature.

In order to obtain a high molecular polyoxyalkylene compound having not less than 90% by weight of polyoxyalkylene glycol in the molecule and having a given kinematic viscosity, it is necessary to effect an addition polymerization of alkylene oxide to an active hydrogen-containing compound so that the addition amount of alkylene oxide to the active hydrogen-containing compound is not less than 90% by weight. The properties of the resulting high molecular weight polyoxyalkylene compound are not substantially influenced by the active hydrogen-containing compound and the terminal OH group, but depend upon the composition of the PAG. The viscosity index of hydraulic oil is improved by the use of the high molecular weight polyoxyalkylene compound.

In the present invention, the high molecular weight polyoxyalkylene compound having 15–80% by weight, preferably 45–60% by weight, of oxyethylene based on the total oxyalkylene and further having a solidifying point of not higher than 0°C is used. The reason is that, when the oxyethylene content and the solidifying point of the polyoxyalkylene compound are outside the above limited ranges, the resulting hydraulic oil is solidified at low temperature, is poor in the fluidity and has a high viscosity at low temperature.

The reason why 2–40 parts by weight of the high molecular weight polyoxyalkylene compound is added to 100 parts by weight of the mixture of compound (1) and at least one of compounds (2) and (3) is that less than 2 parts by weight of the addition amount of high molecular weight polyoxyalkylene compound can not satisfactorily increase the viscosity index of the resulting hydraulic oil, and more than 40 parts by weight of the addition amount of the polyoxyalkylene compound decreases the low temperature viscosity characteristics and the fluidity of the resulting hydraulic oil, and further lowers the wet equilibrium reflux boiling point thereof.

The hydraulic oil of the present invention satisfies all the properties required for the base fluid of brake hydraulic oil, which are defined in DOT-3 Standard.

Further, the hydraulic oil of the present invention satisfies the properties required for the base fluid of hydraulic oil of suspension (schok absorber) defined in MIL-L-15,017, No. 2,075H Standard, and the properties required for the base fluid of ATF defined in DEXRON Standard.

The hydraulic oil of the present invention can be added with antifoaming agent antioxidant, abrasion-preventing agent, anticorrosive or oiliness-improving agent depending upon the use purpose so that the properties of the oil can satisfy standard values for hydraulic oil.

The following examples are given for the purpose of illustration of this invention and are not intended as limitations thereof. In the examples, "part" and "%" means by weight unless otherwise specified.

EXAMPLE 1

To 32 parts (1.0 mol) of methanol was added 0.2 parts of sodium hydroxide, and an addition polymerization of a mixture composed of 105 parts (2.39 moles) of EO and 35 parts (0.60 mole) of PO (EO/PO = 75/25) to the methanol was effected at 80°–120°C under a pressure of 0.5–5.0 Kg/cm$^2$ in nitrogen gas to obtain 171 parts of crude polyoxyethylenepropylene glycol monomethyl ether (hereinafter referred to as crude EPGmME-1).

Then, 171 parts of the crude EPGmME-1 was added with 1.0 parts of activated clay, and dehydrated at 60°–90°C for 1 hour under a reduced pressure of 50 mmHg in nitrogen gas to obtain 165 parts of purified EPGmME-1, which had an OH value of 325 and an average molecular weight (MW) of 173.

To 171 parts of the above obtained crude EPGmME-1 was added 24.5 parts (0.45 mole) of sodium methylate, and the resulting mixture was heated at 70°–120°C for 1 hour under a reduced pressure of 50 mmHg in nitrogen gas to convert the terminal OH group into sodium salt by converting the methylate into methanol. Methyl chloride gas was introduced into the reaction system at this temperature to methyl-etherify the EPGmME-1 until the alkali value of the reaction product was not higher than 0.1.

The reaction product was filtered to obtain 169 parts of a polyoxyethylene-propylene glycol monomethyl-dimethyl ether mixture(EPMdME-1) having an OH value of 165 and a diether content of 47%.

The terminal OH group of 171 parts of the crude EPGmME-1 was converted into sodium salt under the same condition as described above, and then 18.7 parts (0.22 mole) of methylene chloride was added dropwise to the reaction system, and the resulting mixture was heated at 80°–140°C for 3 hours to effect a methyl-etherification reaction, filtered and purified to obtain 167 parts of a polyoxyethyleneprpylene glycol monomethyl-dimethyl ether mixture (EPMdME-2) having an OH value of 179 and a diether content of 45%.

EXAMPLE 2

An addition polymerization of a mixture of 94.3 parts (2.14 moles) of EO and 50.7 parts (0.88 mole) of PO (EO/PO = 65/35) to 32 parts (1.0 mole) of methanol was effected in the same manner as described in Example 1, and the catalyst was filtered off to obtain 170 parts of polyoxyethylene-propylene glycol monomethyl ether (EPGmME-2) having an OH value of 315 and a MW of 178.

To 176 parts of crude EPGmME-2 was added 5.4 parts (0.1 mole) of sodium methylate to convert the OH group into sodium salt by converting the methylate into methanol, and then methyl chloride gas was introduced into the reaction system to methyl etherify the EPGmME-2, and the reaction product was purified to obtain 171 parts of a monomethyldiethyl ether mixture (EPMdME-2) having a OH value of 275 and a diether content of 12%.

EXAMPLE 3

To 46.1 parts (1.0 mole) of ethanol were added forcedly under pressure 175 parts (3.97 moles) of EO, 37.5 parts (0.65 mole) of PO and 37.5 parts (0.52 mole) of BO (BO is a mixture of 1.2-/2.3- of 8/2) (EO:-PO:BO = 70:15:15) to effect a block addition polymerization of EO, PO and BO to the methanol in the same manner as described in Example 1, and the catalyst was filtered off to obtain 287 parts of polyoxyethylene-propylene-butylene glycol monoethyl ether (EPBGmEE-1) having a OH value of 193 and a MW of 291.

To 290 parts of crude EPBmEE-1 was added 22.7 parts (0.42 mole) of sodium methylate to convert the OH group into sodium salt by converting the methylate into methanol, and then 29.0 parts (0.45 mole) of ethyl chloride was added dropwise to the reaction system to ethyl-therify the EPBGmEE-1, and the reaction product was purified to obtain 288 parts of a monoethyl-diethyl ether mixture (EPBMdEE-1) having an OH value of 105 and a diether content of 43%.

COMPARATIVE EXAMPLE

An addition polymerization of a mixture of 56 parts (1.25 moles) of EO and 104 parts (1.79 moles) of PO (EO/PO = 35/65) to 32 parts (1.0 mole) of methanol was effected in the same manner as discribed in Example 1, and the polymerization reaction product was purified to obtain 181 parts of polyoxyethylene-propylene glycol monomethyl ether (hereinafter referred to as Comparative EPGmME-1) having an OH value of 298 and a MW of 188.

To 189 parts of crude Comparative EPGmME-1 was added 22.7 parts (0.42 mole) of sodium methylate to convert the OH group into sodium salt, and then methyl chloride gas was introduced into the reaction system to methyl-etherity Comparative EPGmME-1, and the reaction product was filtered to obtain 183 parts of a monomethyl-dimethyl ether mixture (Comparative EPMdME-1) having an OH value of 159 and a diether content of 45%.

Next, methods for producing high molecular weight polyoxyalkylene compounds having a kinematic viscosity of at least 8 cst at 210°F will be explained.

EXAMPLE 4

To 1 part of n-butanol was added 0.04 part of potassium hydroxide, and an addition polymerization of 6.8 parts of EO and 6.8 parts of PO (EO/PO = 50/50) to the n-butanol was effected at 80°–120°C under a pressure of 0.5–5.0 Kg/cm² in nitrogen gas for 8 hours. The reaction product was neutralized with hydrochloric acid, and 15 parts of toluene was added thereto, and the mass was washed with 20 parts of warm water at 60°–90°C. The mass was then heated under pressure to remove the toluene, and filtered to remove the resulting potassium chloride and to obtain 14.1 parts of polyoxyethylene-propylene glycol monobutyl ether (EPGmBE-1) having an OH value of 53.5, a MW of 1,050 and a kinematic viscosity of 11.3 cst at 210°F.

To 1 part of n-butanol was added 0.15 part of potassium hydroxide, and then an addition polymerization of 30 parts of EO and 30 parts of PO (EO/PO = 50/50) to the n-butanol was effected in the same manner as described above. The reaction product was purified with 70 parts of toluene and 100 parts of warm water to obtain 59 l parts of EPGmBE-2 having an OH value of 19.5, a MW of 2,880 and a kinematic viscosity of 73.1 cst at 210°F.

To 28.8 parts of the resulting EPGmBE-2 was added 0.65 part of sodium methylate, and the resulting mixture was heated for 3 hours under a pressure of 50 mmHg in nitrogen gas to convert the OH group into sodium salt by converting the methylate into methanol. Then, methyl chloride was blown into the reaction system at 80°–120°C for 3 hours to methyl-etherify the EPGmBE-2 until the alkali value of the reaction product was not higher than 0.1. The reaction product was purified with 30 parts of toluene and 50 parts of warm water to obtain 28 parts of polyoxyethylene-propylene glycol butyl methyl ether (EPGBME-1) having an OH value of 2.1 and a kinematic viscosity of 63.7 cst at 210°F.

28.8 parts of EPGmBE-2 was etherified by using 0.54 parts of sodium methylate and 0.43 part of methylene chloride, and the reaction product was purified to obtain 27.5 parts of polyoxyethylene-propylene glycol dibutyl ether (EPGdBE-1) having an OH value of 2.9 and a kinematic viscosity of 124 cst at 210°F.

To 10.5 parts of crude EPGmBE-1 was added 0.1 part of potassium hydroxide as a catalyst, and an addition polymerization of 350 parts of EO and 350 parts of PO (EO/PO = 50/50) to the EPGmBE-1 was effected in the same manner as described above, and the reaction product was purified to obtain 706 parts of EPGmBE-3 having an OH value of 7.9, a MW of 7,120 and a kinematic viscosity of 1,950 cst at 210°F.

EXAMPLE 5

To 1 part of ethylene glycol was added 0.09 part of potassium hydoxide, and an addition polymerization of a mixture of 42 parts of EO and 28 parts of PO (EO/PO = 60/40) to the ethlene glycol was effected under the same condition as described in Example 4, and the reaction product was purified to obtain 65 parts of polyoxyethylene-propylene glycol (EPG:1) having an OH value of 30.5, a MW of 3,650 and a kinematic viscosity of 53.8 cst at 210°F.

EXAMPLE 6

To 1 part of glycerine was added 0.05 part of potassium hydroxide, and an addition polymerization of a mixture of 18.5 parts of EO, 7.2 parts of PO and 2.9 parts of BO (EO:PO:BO = 65:25:10) to the glycerine was effected under the same condition as described in Example 4, and the reaction product was purified to obtain 28.2 parts of polyoxyethylene-propylene-butylene glycerine (EPBGl-1) having an OH value of 25.2, a MW of 2,230 and a kinematic viscosity of 31.9 cst at 210°F.

Further, 0.05 part of potassium hydroxide as a catalyst was added to 22.3 parts of crude EPBGl-1, and an addition polymerization of a mixture of 208 parts of EO, 80 parts of PO and 32 parts of BO (EO:PO:BO = 55:25:10) to the EPGl-1 was effected in the same manner as described above, and the reaction product was purified to obtain 340 parts of EPBGl-2 having an OH value of 10.2, a MW of 15,200 and a kinematic viscosity of 2,160 cst at 210°F.

The physical properties of the above obtained high molecular weight polyoxyalkylene compounds are shown in the following Table 1 together with the physical properties of polyoxyethylene glycols PEG-1 NO. 1,000 and PEG-2 NO. 6,000, and polyoxypropylene glycol PPG-1 No. 2,000, which are used as a comparative high molecular weight polyoxyalkylene compound in the following Examples.

EXAMPLE 7

The following Table 2 shows the composition and physical properties of hydraulic oils prepared from low molecular weight PAG ethers of Example 1 and the high molecular weight polyoxyalkylene compounds of Example 4.

Sample Nos. 1–6 are Comparative hydraulic oils and sample Nos. 7–10 are hydraulic oils of the present invention. The hydraulic oil of the present invention is superior to the comparative hydraulic oil in the following points.

1. The hydraulic oil of the present invention is higher in viscosity at high temperature and is lower in the viscosity at low temperature than the comparative hydraulic oil.
2. The hydraulic oil of the present invention is higher in the boiling point and is smaller in the boiling point depression due to water than the comparative hydraulic oil.
3. The hydraulic oil of the present invention is lower than the comparative hydraulic oil in the compatibility with rubber (swelling action on rubber is low). Therefore, the hydraulic oil of the present invention is excellent as a brake oil and satisfies DOT-3 Standard In U.S.A.

Standard values related to the properties of base fluid of hydraulic oil defined in DOT-3 Standard are shown in the following table.

Table 1

| High molecular weight polyoxyalkylene compound | | EO:PO:BO | Average molecular weight | Kinematic viscosity (210°F)(cst) |
|---|---|---|---|---|
| Example 4 | EPGmBE-1 | 50:50:0 | 1,050 | 11.3 |
| Example 4 | EPGmBE-2 | 50:50:0 | 2,880 | 73.1 |
| Example 4 | EPGBME-1 | 50:50:0 | *2,890 | 63.7 |
| Example 4 | EPGdBE-1 | 50:50:0 | *5,600 | 124 |
| Example 4 | EPGmBE-3 | 50:50:0 | 7,120 | 1,950 |
| Example 5 | EPG-1 | 60:40:0 | 3,650 | 53.8 |
| Example 6 | EPBGl-1 | 65:25:10 | 2,230 | 31.9 |
| Example 6 | EPBGl-2 | 65:25:10 | 15,200 | 2,160 |
| Comparative high molecular weight polyether | PEG-1(No. 1,000) | 100:0:0 | 1,015 | 17.5 |
| | PEG-2(No. 6,000) | 100:0:0 | 7,030 | 819 |
| | PPG-1(No. 2,000) | 0:100:0 | 2,080 | 23.4 |

Note: *estimated value

| | Standard | Remarks |
|---|---|---|
| Kinematic viscosity (210°F) (cst) | not less than 1.5 | |
| Kinematic viscosity (−40°C) (cst) | not more than 1,500 | |
| Boiling point (DER) (°C) | not lower than 205 | dry equilibrium reflux boiling point |
| Boiling point (WER) (°C) | not lower than 140 | wet equilibrium reflux boiling point |
| Swelling action on rubber (mm) | 0.15 ~ 1.40 | rubber cup (SBR) for brake 120°C × 70hrs |

The following Table 3 shows the composition and physical properties of hydraulic oils prepared by compounding the low molecular weight PAG ethers of Examples 1 and 2 and Comparative Example to the high molecular weight polyoxyalkylene compounds of Examples 4, 5 and 6 or the comparative high molecular weight polyoxyalkylene compounds. It can be seen from Table 3 that the hydraulic oil of the present invention (sample Nos. 18–20) is superior to the comparative hydraulic oil (sample Nos. 12–17) in the properties as a brake oil.

Table 2

| Composition and physical property | | Comparative hydraulic oil (Sample No.) | | | | | | Hydraulic oil of the present invention (Sample No.) | | | |
|---|---|---|---|---|---|---|---|---|---|---|---|
| | | 1 | 2 | 3 | 4 | 5 | 6 | 7 | 8 | 9 | 10 |
| Low molecular weight PAG ether | EPGmME-1(Example 1)(part) | 100 | — | — | 100 | — | — | 49 | 61.8 | 49 | 76.7 |
| | EPMdME-1(Example 1)(part) | — | 100 | — | — | 100 | — | 51 | 38.2 | — | 23.3 |
| | EPMdME-2(Example 1)(part) | — | — | 100 | — | — | 100 | — | — | 51 | — |
| | PAG monoether content (%) | 100 | 53 | 55 | 100 | 53 | 55 | 76 | 82 | 87 | 89 |
| | PAG diether content (%) | — | 47 | 45 | — | 47 | 45 | 24 | 18 | 13 | 11 |
| | $R_1$ | methyl | methyl | methyl | methyl | methyl | methyl | methyl | methyl | methyl | methyl |
| | $R_2$ | — | methyl | methyl | — | methyl | methyl | methyl | methyl | methyl | methyl |
| | m(EO+PO+BO) | 2.99 | 2.99 | 2.99 | 2.99 | 2.99 | 2.99 | 2.99 | 2.99 | 2.99 | 2.99 |
| | EO:PO:BO | 75:25:0 | 75:25:0 | 75:25:0 | 75:25:0 | 75:25:0 | 75:25:0 | 75:25:0 | 75:25:0 | 75:25:0 | 75:25:0 |
| High molecular weight polyoxyalkylene compound | EPGmBE-1(Example 4)(part) | — | — | — | 23.0 | — | — | 23.0 | — | — | — |
| | EPGmBE-2(Example 4)(part) | — | — | — | — | 20.0 | — | — | 20.0 | — | — |
| | EPGBME-1(Example 4)(part) | — | — | — | — | — | 20.0 | — | — | — | — |
| | EPGdBE-1(Example 4)(part) | — | — | — | — | — | — | — | — | 16.0 | — |
| | EPGmBE-3(Example 4)(part) | — | — | — | — | — | — | — | — | — | 7.5 |
| Physical | Kinematic viscosity | | | | | | | | | | |

Table 2-continued

| Composition and physical property | | Comparative hydraulic oil (Sample No.) | | | | | | Hydraulic oil of the present invention (Sample No.) | | | |
|---|---|---|---|---|---|---|---|---|---|---|---|
| | | 1 | 2 | 3 | 4 | 5 | 6 | 7 | 8 | 9 | 10 |
| properties of hydraulic oil | 210°F (cst) | 1.47 | 1.28 | 1.79 | 2.59 | 3.09 | 3.94 | 2.56 | 3.24 | 4.32 | 4.57 |
| | −40°C (cst) | 431 | 189 | 529 | 1885 | 1310 | 1405 | 1210 | 1360 | 1445 | 1430 |
| | Boiling point DER (°C) | 218 | 230 | 235 | 223 | 232 | 235 | 228 | 226 | 230 | 225 |
| | containing 3.5% water (°C) | 145 | 138 | 139 | 143 | 138 | 137 | 143 | 142 | 141 | 142 |
| | Swelling action on rubber SBR (mm) | 1.06 | 1.97 | 1.60 | 0.95 | 1.61 | 1.41 | 1.12 | 1.09 | 0.93 | 1.10 |

Table 3

| Composition and physical property | | Comparative hydraulic oil (Sample No.) | | | | | | Hydraulic oil of the present invention (Sample No.) | | | |
|---|---|---|---|---|---|---|---|---|---|---|---|
| | | 11 | 12 | 13 | 14 | 15 | 16 | 17 | 18 | 19 | 20 |
| Low molecular weight PAG ether | EPGmME-1(Example 1)(part) | — | — | — | — | — | 76.7 | — | — | — | — |
| | EPMdME-1(Example 1)(part) | — | — | — | — | — | 23.3 | — | — | — | — |
| | EPMdME-2(Example 2)(part) | 100 | — | — | 100 | 100 | — | — | 100 | 100 | 100 |
| | Comparative EPGmME-1 (Comparative Example) (part) | — | 100 | — | — | — | — | 71.1 | — | — | — |
| | Comparative EPMdME-1 (Comparative Example) (part) | — | — | 100 | — | — | — | 28.9 | — | — | — |
| | PAG monoether content (%) | 88 | 100 | 55 | 88 | 88 | 89 | 87 | 88 | 88 | 88 |
| | PAG diether content (%) | 12 | — | 45 | 12 | 12 | 11 | 13 | 12 | 12 | 12 |
| | $R_1$ | methyl | methyl | methyl | methyl | methyl | methyl | methyl | methyl | methyl | methyl |
| | $R_2$ | methyl | — | methyl | methyl | methyl | methyl | methyl | methyl | methyl | methyl |
| | m(EO+PO+BO) | 3.02 | 3.04 | 3.04 | 3.02 | 3.02 | 2.99 | 3.04 | 3.02 | 3.02 | 3.02 |
| | EO:PO:BO | 65:35:0 | 35:65:0 | 35:65:0 | 65:35:0 | 65:35:0 | 75:25:0 | 35:65:0 | 65:35:0 | 65:35:0 | 65:35:0 |
| High molecular weight polyoxyalkylene compound | EPGmPE-3(Example 4)(part) | — | — | — | — | — | — | — | — | — | 8.0 |
| | EPG-1 (Example 5)(part) | — | — | — | — | — | — | — | 20.0 | — | — |
| | EPGl-1 (Example 6)(part) | — | — | — | — | — | — | 16.0 | — | — | — |
| | EPGGl-2 (Example 6)(part) | — | — | — | — | — | — | — | — | 6.5 | — |
| | PEG-1 (No. 1,000) (Comparative polyoxyalkylene compound)(part) | — | — | — | 23.0 | — | — | — | — | — | — |
| | PEG-2 (No. 6,000) (Comparative polyoxyalkylene compound)(part) | — | — | — | — | — | 7.5 | — | — | — | — |
| | PPG-1 (No. 2,000) (Comparative polyoxyalkylene compound)(part) | — | — | — | — | 20.0 | — | — | — | — | — |
| Physical properties of hydraulic oil | Kinematic viscosity 210°F (cst) | 1.45 | 1.60 | 1.39 | 2.85 | 2.97 | 4.21 | 3.46 | 3.16 | 4.35 | 4.54 |
| | −40°C (cst) | 306 | 668 | 249 | solidified | 1870 | solidified | 1380 | 1290 | 1440 | 1405 |
| | Boiling point DER (°C) | 231 | 227 | 234 | 233 | 232 | 225 | 235 | 234 | 232 | 233 |
| | containing 3.5% water (°C) | 145 | 129 | 123 | 143 | 125 | 143 | 124 | 142 | 141 | 141 |
| | Swelling action on rubber SBR (mm) | 1.11 | 1.42 | 2.25 | 0.89 | 1.61 | 0.98 | 1.66 | 0.98 | 1.04 | 1.02 |

EXAMPLE 8

Hydraulic oil sample No. 8 or No. 20 was used as a base fluid, and various additives were compounded to the hydraulic oil according to the following compounding recipe to prepare brake oil sample No. 8-1 or No. 20-1.

| Brake oil sample No. 8-1 | Part |
|---|---|
| Hydraulic oil sample No. 8 (base fluid) | 100.000 |
| Dioctylphenylamine (antioxidant) | 0.50 |
| Benzotriazole (anticorrosive) | 0.05 |
| Diethanolamine | 1.00 |
| (PH regulator) Silicone oil (antifoaming agent) (Silicone KS-66, made by Shinetsu Kagaku Co.) | 0.001 |

Brake oil sample No. 20-1 was prepared in the same compounding recipe.

The resulting brake oil samples No. 8-1 and No. 20-1 were tested according to DOT-3 Standard. The following Tables 4-1 and 4-2 show that brake oil sample No. 8-1 and No. 20-1 satisfy all of the standard values defined in DOT-3 Standard.

Table 4-1

|  | Standard value | Brake oil (Sample No.) 8 - 1 | Brake oil (Sample No.) 20 - 1 |
|---|---|---|---|
| Kinematic viscosity (210°F)(cst) | not less than 1.5 | 3.26 | 4.55 |
| kinematic viscosity (−40°C)(cst) | not more than 1,500 | 1,385 | 1,450 |
| Flash point (°C) | not lower than 82 | 129 | 132 |
| Boiling point (DER)(°C) | not lower than 205 | 227 | 233 |
| Boiling point (WER)(°C) | not lower than 140 | 143 | 142 |
| Water content (%) | — | 3.3 | 3.4 |
| PH | 7.0 ~ 11.5 | 8.1 | 8.3 |
| Heat stability (variation of boiling point)(°C) | within 3.0 | −1.5 | 1.0 |
| Chemical stability (variation of boiling point) (°C) | within 3.0 | 0 | −0.5 |
| Corrosive action on metal (mg/cm²) | | | |
| Tin plate | within 0.2 | −0.09 | −0.08 |
| Steel | within 0.2 | −0.02 | −0.01 |
| Aluminum | within 0.1 | −0.02 | −0.01 |
| Cast iron | within 0.2 | −0.02 | −0.01 |
| Brass | within 0.4 | −0.18 | −0.15 |
| Copper | within 0.4 | −0.12 | −0.13 |
| Appearance of the metal | no pitching and etching | no | no |
| Property after test | | | |
| PH | 7.0 ~ 11.5 | 7.6 | 7.7 |
| Jellifying of oil | no | no | no |
| Formation of crystals | no | no | no |
| Precipitate (%) | not more than 0.1 | 0.01 | 0.02 |
| Low temperature characteristics (temp×hrs) | −40°C×44hrs  −50°C×6hrs | −40°C×44hrs  −50°C×6hrs | −40°C×44hrs  −50°C×6hrs |
| Hiding power (identification of boundary line of test paper) | clearly identified | clearly identified | clearly identified |
| Separation and precipitation | no | no | no |
| Time until foams reach oil surface (sec) | within 10    within 35 | 2    7 | 1    6 |

Table 4-2

|  | Standard value | Brake oil (Sample No.) 8 - 1 | Brake oil (Sample No.) 20 - 1 |
|---|---|---|---|
| Evaporability | | | |
| Evaporation loss (%) | not more than 80 | 53 | 55 |
| Property of residue | | | |
| Sandish and abrasive precipitate | no | no | no |
| Fluidizing point (°C) | not higher than −5 | −8 | −10 |
| Water resistance (−40°C, 24hrs) | | | |
| Hiding power (identification of boundary line of test paper) | clearly identified | clearly identified | clearly identified |
| Separation and precipitation | no | no | no |
| Time until foams reach oil surface (sec) | within 10 | 3 | 2 |
| Water resistance (−40°C, 24hrs) | | | |
| Separation | no | no | no |
| Precipitate (separation by centrifuge) (vol%) | 0.05 | 0.02 | 0.01 |
| Resistance to oxidation | | | |
| Pitching and etching (Al and cast iron) | no | no | no |
| Formation of rubbery material (metal surface) | no | no | no |
| Weight change of test metal (mg/cm²) | | | |
| Aluminum | not more than 0.05 | −0.01 | −0.01 |
| Cast iron | not more than 0.30 | −0.01 | 0 |
| Swelling action on rubber (SBR, 70°C, 120hrs) | | | |
| Swelling (increase of the diameter of base rubber)(mm) | 0.15 ~ 1.40 | 1.01 | 0.93 |
| Hardness IRHD (degree) | not more than 10 | 2 | 3 |
| Collapse | no | no | no |
| Swelling action on rubber (SBR, 120°C, 70hrs) | | | |
| Swelling (increase of the diameter of base rubber)(mm) | 0.15 ~ 1.40 | −1.05 | 0.98 |
| Hardness IRHD (degree) | not more than 15 | 3 | 3 |
| Collapse | no | no | no |

EXAMPLE 9

The hydraulic oil of the present invention has excellent properties to be used as hydraulic oils of shock absorber, autotransmission and the like.

Table 5 shows the composition and physical properties of hydraulic oils prepared from the low molecular weight PAG ethers of Example 3 and the high molecular weight polyoxyalkylene compounds of Examples 4 and 5.

Table 5

| Composition and physical property | | Comparative hydraulic oil (Sample No.) 21 | Comparative hydraulic oil (Sample No.) 22 | Hydraulic oil of the present invention (Sample No.) 23 | Hydraulic oil of the present invention (Sample No.) 24 | Hydraulic oil of the present invention (Sample No.) 25 |
|---|---|---|---|---|---|---|
| Low | EPBGmEE-1 (Example 3)(part) | 100 | — | 76.8 | 65.1 | 53.5 |

Table 5-continued

| Composition and physical property | | Comparative hydraulic oil (Sample No.) | | Hydraulic oil of the present invention (Sample No.) | | |
|---|---|---|---|---|---|---|
| | | 21 | 22 | 23 | 24 | 25 |
| molecular weight PAG ether | EPBBMdEE-1(Example 3)(part) | — | 100 | 23.2 | 34.9 | 46.5 |
| | PAG monoether content (%) | 100 | 57 | 90 | 85 | 80 |
| | PAG diether content (%) | — | 43 | 10 | 15 | 20 |
| | $R_1$ | ethyl | ethyl | ethyl | ethyl | ethyl |
| | $R_2$ | — | ethyl | ethyl | ethyl | ethyl |
| | m(EO+PO+BO) | 5.14 | 5.14 | 5.14 | 5.14 | 5.14 |
| | EO:PO:BO | 70:15:15 | 70:15:15 | 70:15:15 | 70:15:15 | 70:15:15 |
| High molecular weight polyoxyalkylene compound | EPGmBE-2 (Example 4)(part) | — | — | 28 | 30 | — |
| | EPG-1 (Example 5)(part) | — | — | — | — | 32 |
| Physical properties of hydraulic oil | Kinematic viscosity | | | | | |
| | 210°F (cst) | 3.34 | 2.55 | 7.63 | 7.81 | 7.71 |
| | 130°F (cst) | 8.19 | 6.37 | 16.9 | 17.1 | 16.3 |
| | 0°F (cst) | 181 | 129 | 789 | 802 | 775 |
| | Absolute viscosity | | | | | |
| | −10°F (cp) | 437 | 253 | 1634 | 1711 | 1592 |
| | −40°F (cp) | 3810 | 1510 | 10315 | 12100 | 9368 |
| | Fluidizing point (°C) | −57 | −56 | −48 | −49 | −48 |
| | Flash point (°C) | 171 | 173 | 182 | 179 | 177 |
| | Carbon residue (%) | 0.01 | 0.02 | 0.01 | 0.01 | 0.02 |
| | Swelling action on rubber (buna N, 300°F, 70 hrs.) | | | | | |
| | Percentage in volumetric change(vol%) | 8.5 | 7.3 | 2.9 | 3.3 | 3.5 |
| | Hardness | −19 | −6 | −3 | −3 | −4 |

For comparison, standard values related to the properties required for the base fluids of shock absorber hydraulic oil defined in MIL-L-15, 017, No. 2,075H Standard and of ATF defined in DEXRON Standard are shown in the following table.

| | Standard value | |
|---|---|---|
| | Shock absorber hydraulic oil (MIL-L-15,017, No. 2,075H Standard)) | AFT (DEXRON Standard) |
| Kinematic viscosity | | |
| 210°F (cst) | — | not less than 7.0 |
| 130°F (cst) | 13.07 to 18.16 | — |
| 0°F (cst) | not more than 2,179 | — |
| Absolute viscosity | | |
| −10°F (cp) | — | not more than 4,000 |
| −40°F (cp) | — | not more than 55,000 |
| Fluidizing point (°C) | not higher than −28.9 | — |
| Flash point (°C) | not lower than 157.2 | not lower than 160 |
| Carbon residue (%) | not more than 0.1 | — |
| Swelling action on rubber (buna N, 300°F, 70 hrs.) | | |
| Percentage of volumetric change (vol%) | — | 1–5 |
| Hardness | — | 0 to −5 |

What is claimed is:

1. A hydraulic oil composition comprising 100 parts by weight of a mixture of 60–98% by weight of a polyoxyalkylene glycol monoalkyl ether having the following general formula (1) and 2–40% by weight of at least one of polyoxyalkylene glycol dialkyl ethers having the following general formulae (2) and (3), $$R^1O(C_mH_{2m}O)_nH, \quad (1)$$

$$R^1O(C_mH_{2m}O)_nR^2 \quad (2)$$

and $$[R^1O(C_mH_{2m}O)_n]_2CH_2 \quad (3)$$

wherein $R^1$ and $R^2$ represent alkyl groups having 1–3 carbon atoms respectively, $C_mH_{2m}O$ represents an oxyalkylene group, m represents a positive integer of 2, 3 or 4, and n represents a positive integer of 2–6, the oxyethylene content in the total oxyalkylene of compounds (1), (2) and (3) being 40–90% by weight, and 2–40 parts by weight of a high molecular weight polyoxyalkylene compound having a kinematic viscosity of at least 8 cst at 210°F and having not less than 90% by weight of polyoxyalkylene glycol in the molecule and 15–80% by weight of oxyethylene based on the total oxyalkylene in the molecule.

2. A hydraulic oil composition according to claim 1, wherein said high molecular weight polyoxyalkylene compound has a kinematic viscosity of 20–50,000 cst at 210°F.

3. A hydraulic oil composition according to claim 1, wherein said high molecular weight polyoxyalkylene compound has a solidifying point of not higher than 0°C.

4. A hydraulic oil composition according to claim 1, wherein said high molecular weight polyoxyalkylene compound has 45–60% by weight of oxyethylene based on the total oxyalkylene in the molecule.

* * * * *